United States Patent
Verma (10) Patent No.: US 9,414,783 B2
(45) Date of Patent: Aug. 16, 2016

(54) FORCE ASSESSMENT DEVICE AND METHOD FOR LEAD EXTRACTION

(71) Applicant: Atrial Systems, LLC, Pensacola, FL (US)

(72) Inventor: Sumit Verma, Pensacola, FL (US)

(73) Assignee: Atrial Systems, LLC, Pensacola, FL (US)

( * ) Notice: Subject to any disclaimer, the term of this patent is extended or adjusted under 35 U.S.C. 154(b) by 0 days.

(21) Appl. No.: 14/691,357

(22) Filed: Apr. 20, 2015

(65) Prior Publication Data

US 2015/0223754 A1 Aug. 13, 2015

Related U.S. Application Data

(62) Division of application No. 12/392,944, filed on Feb. 25, 2009, now Pat. No. 9,032,806.

(60) Provisional application No. 61/066,798, filed on Feb. 25, 2008.

(51) Int. Cl.
| | |
|---|---|
| *G01B 5/30* | (2006.01) |
| *A61B 5/00* | (2006.01) |
| *A61N 1/05* | (2006.01) |
| *G01L 5/00* | (2006.01) |
| *A61B 19/00* | (2006.01) |

(52) U.S. Cl.
CPC ............... *A61B 5/4851* (2013.01); *A61N 1/05* (2013.01); *G01L 5/0028* (2013.01); *A61B 2019/464* (2013.01); *A61B 2562/0261* (2013.01)

(58) Field of Classification Search
CPC . A61B 2562/0261; A61N 1/05; G01L 5/0028
USPC .............................................. 73/760, 768, 781
See application file for complete search history.

(56) References Cited

U.S. PATENT DOCUMENTS

| | | | | |
|---|---|---|---|---|
| 5,779,715 | A * | 7/1998 | Tu | A61B 17/50 606/108 |
| 6,033,402 | A * | 3/2000 | Tu | A61B 18/1492 606/41 |
| 8,326,437 | B2 * | 12/2012 | Cully | A61N 1/05 607/116 |
| 8,986,228 | B2 * | 3/2015 | Auchinleck | A61B 5/1036 128/882 |
| 2002/0123785 | A1 * | 9/2002 | Zhang | A61N 1/056 607/126 |
| 2004/0127889 | A1 * | 7/2004 | Zhang | 606/1 |

* cited by examiner

*Primary Examiner* — Max Noori
(74) *Attorney, Agent, or Firm* — Faegre Baker Daniels LLP (57) ABSTRACT

A force assessment device and a method for lead extraction are provided. A force gauge is configured to measure a traction force, and a strain gauge that is configured to measure a countertraction force. An interface is communicatively coupled to the force gauge and the strain gauge, and the interface is configured to present data regarding at least one of the traction force and the countertraction force.

20 Claims, 9 Drawing Sheets

FORCE ASSESSMENT DEVICE AND METHOD FOR LEAD EXTRACTION

The present application is a divisional of prior U.S. application Ser. No. 12/392,944, filed Feb. 25, 2009, entitled FORCE ASSESSMENT DEVICE AND METHOD FOR LEAD EXTRACTION, which claims the benefit of U.S. Provisional Application No. 61/066,798, filed Feb. 25, 2008, both of which are hereby incorporated by reference in their entirety.

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

The field of the invention relates generally to systems and methods for surgery and, more particularly, to systems and methods for extracting an object embedded in a biological tissue.

A pacemaker is a surgically implanted device that maintains a heart beat at a regular rate. A lead is a wire that couples a pacemaker or an implantable cardioverter defibrillator (ICD) to a heart muscle. A lead extraction is the removal of at least one lead from heart tissue. Endocardial lead extraction may be necessary when at least one of the leads is not working properly. Known causes of lead failure include fracture or other damage to the lead, infection at a site of the lead and/or lead implant, and "exit block," which occurs when a lead requires more energy to properly function than the pacemaker or ICD can deliver. At least some known methods for endocardial lead extraction are complicated, time-consuming procedures that are associated with significant risk.

Known methods for endocardial lead extraction include using a locking stylet to apply traction force to a body of a lead. More specifically, the locking stylet is coupled to the lead and is manually pulled until the lead is extracted from the heart tissue. Moreover, some known methods require additional force and include using an extraction sheath to apply countertraction force about the body of the lead. More specifically, the sheath slides about the lead and is manually pushed into the scar tissue adhesions.

The combined use of a traction and a countertraction force facilitates shearing the scar tissue adhesions from the lead with a reduced amount of damage to the cardiac tissue surrounding the lead. The combined use of traction force and countertraction force is relatively complicated, and success is highly dependent on the skill and experience of the physician. Known issues related to excess traction and/or countertraction forces include lead damage, arrhythmias, low blood pressure, tissue avulsion, hemothorax, tamponade, and even death. Notably, two elements of the combined use is how hard to pull on the locking stylet and how hard to push the extraction sheath.

BRIEF SUMMARY OF THE INVENTION

In one embodiment, a method for lead extraction is provided. The method includes providing a force gauge, measuring a traction force with the force gauge, providing a strain gauge, measuring a countertraction force with the strain gauge, and presenting data regarding at least one of the traction force and the countertraction force.

In another embodiment, a force assessment device is provided. The device includes a force gauge configured to measure a traction force, a strain gauge that is configured to measure a countertraction force, and an interface communicatively coupled to the force gauge and the strain gauge, the interface configured to present data regarding at least one of the traction force and the countertraction force.

DETAILED DESCRIPTION OF THE INVENTION

The systems and methods described herein enable monitoring traction and countertraction forces, thereby reducing the risk of lead damage, tissue avulsion, and heart wall rupture.

Figure 1:
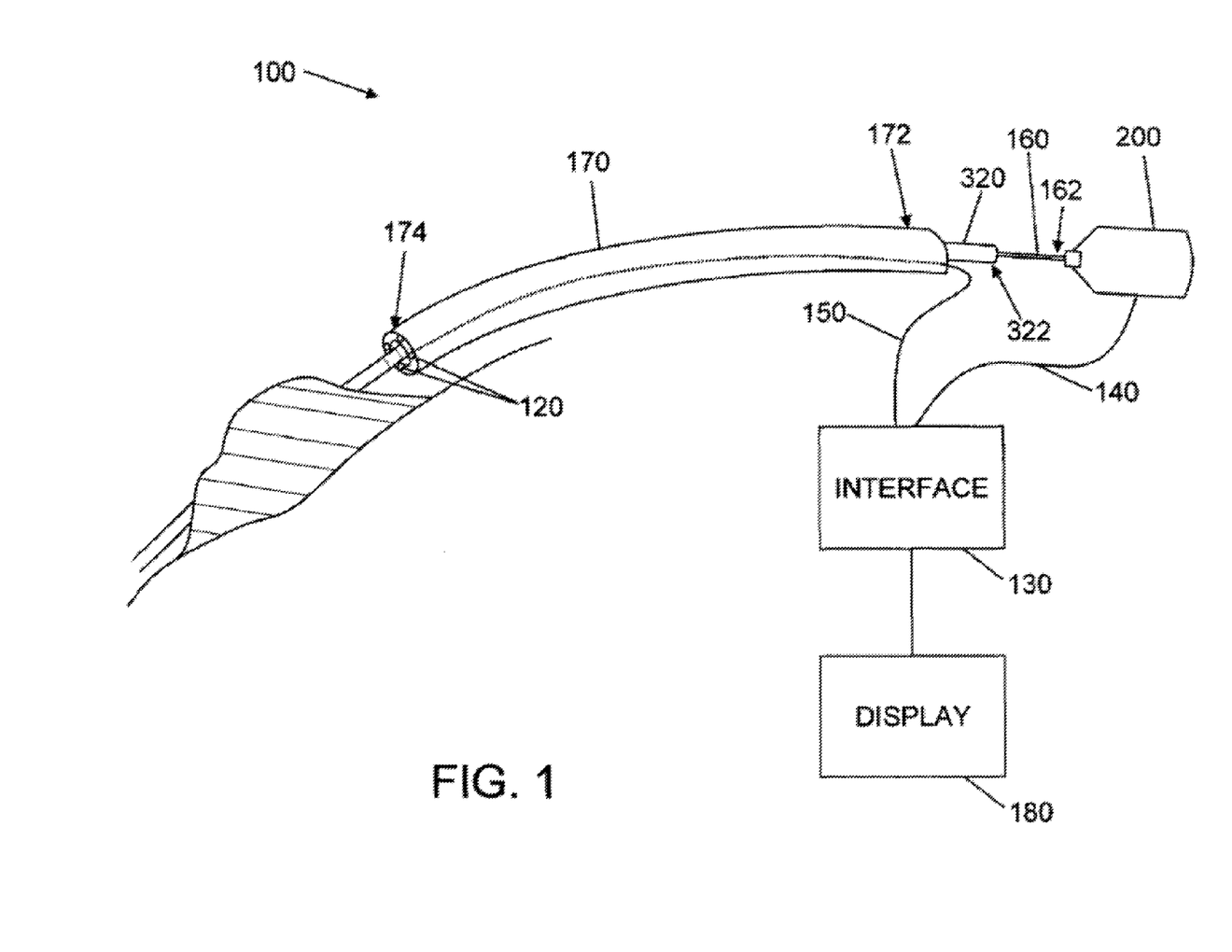
FIG. 1 is a schematic illustration of a force assessment device.

FIG. 1 is a schematic illustration of a force assessment device 100 that includes a force gauge 110, a strain gauge 120, and an interface unit 130 communicatively coupled to force gauge 110 and strain gauge 120.

Force gauge 110 is a mechanical gauge that is configured to provide an assessment of a tension, also known as a traction force. More specifically, force gauge 110 is configured to measure at least one of an absolute force and a relative force applied to a locking stylet 160. In the exemplary embodiment, force gauge 110 is coupled to a proximal end 162 of stylet 160. In alternate embodiments, force gauge 110 is at least one of a fiber optic sensor, a miniature load cell, and a piezoelectric material that is positioned within a shaft (not shown) of stylet 160. Notably, force gauge 110 is not limited to any particular mechanism for measuring a traction force applied to stylet 160.

In the exemplary embodiment, stylet 160 is a thin wire that is inserted into a catheter to maintain rigidity or into a hollow needle to maintain patency. Stylet 160 is coupled to at least a portion of an implanted pacing lead 320. In the exemplary embodiment, stylet 160 is coupled to a distal end 322 of lead 320 to facilitate applying traction without breaking lead 320. In an alternate embodiment, stylet 160 is coupled to an entire length of lead 320.

Strain gauge 120 is at least one pressure sensor that is configured to provide an assessment of a tension, also known as a countertraction force. More specifically, strain gauge 120 is configured to measure at least one of an absolute force and a relative force applied to a lead extraction sheath 170. In the exemplary embodiment, strain gauge 120 is embedded in a distal end 174 of sheath 170 to maintain a smooth atraumatic surface of sheath 170. More specifically, in the exemplary embodiment, strain gauge 120 is comprised of a piezoelectric material. In the exemplary embodiment, the piezoelectric material at distal end 174 of sheath 170 provides a pressure sensitive jacket that is approximately 200 micrometers thick. In one embodiment, strain gauge 120 includes a coaxial sensor design that facilitates providing a single average pressure recording. In another embodiment, strain gauge 120 includes a segmental sensor design that facilitates providing a spatial resolution. In alternate embodiments, strain gauge 120 is at least one of a small diameter extension spring, a fiber optic sensor, and a miniature load cell that is positioned within a shaft (not shown) of sheath 170. Notably, strain gauge 120 is not limited to any particular mechanism of measuring a countertraction force applied to sheath 170.

In the exemplary embodiment, sheath 170 is a plastic tube configured to encompass stylet 160 and/or lead 320. More specifically, in the exemplary embodiment, sheath 170 is configured to dilate a lead-tissue interface 310 about lead 320. In one embodiment, sheath 170 has a length of approximately 30-50 cm, an inner diameter of sheath 170 has a circumference of approximately 7-10 Fr., and an outer diameter of sheath 170 has a circumference of approximately 10-13 Fr. In one embodiment, sheath 170 is configured to transmit a laser and/or RF energy to facilitate dilating or dissecting lead 320 from lead-tissue interface 310. In another embodiment, a handle (not shown) is coupled to a proximal end 172 of sheath 170 and is configured to facilitate advancing and/or rotating sheath 170.

In the exemplary embodiment, interface unit 130 is configured to provide power and/or signals to at least one of force gauge 110, strain gauge 120, and a display 180. Interface unit 130 is communicatively coupled to force gauge 110 and strain gauge 120 via suitable connectors 140 and 150, respectively. More specifically, suitable connector 140 is configured to relay input and/or output signals between force gauge 110 and interface unit 130, and suitable connector 150 is configured to relay input and/or output signals between strain gauge 120 and interface unit 130. In the exemplary embodiment, suitable connector 150 is embedded in sheath 170 and emerges from proximal end 172 of sheath 170. In one embodiment, suitable connectors 140 and 150 extend approximately 4-10 feet from handle device 200 and sheath 170, respectively. In an alternate embodiment, at least one of force gauge 110 and strain gauge 120 is communicatively coupled to interface unit 130 via remote transmission. In the exemplary embodiment, interface unit 130 is a computer that includes one or more processors or processing units (not shown) and a system memory (not shown).

Display 180 is configured to present at least one of an audible signal, a visual signal, and a tactile signal. More specifically, in the exemplary embodiment, display 180 facilitates reducing a probability that at least one of a traction and countertraction force exceeds a predefined limit and/or ratio. For example, a sudden increase and/or decrease in a traction and/or countertraction force may provide the physician with a warning regarding an impending tear in tissue 330. More specifically, a sudden increase in traction force and a sudden change in countertraction force, increase or decrease, are potentially dangerous. In the exemplary embodiment, such situations are categorized in "Alert Category 1." Moreover, while a sudden decrease in traction force decreases an effectiveness of a procedure, it is not necessarily risky for a patient. In the exemplary embodiment, such situations are categorized as "Alert Category 2." Notably, the alert criteria are customizable based upon physician preference and patient characteristics.

In one embodiment, interface unit 130 and display 180 are configured to present a real time image of tissue-lead interface 310. More specifically, in the other embodiment, a transespohageal echo and/or another imaging modality is used to provide a two-dimensional and/or a three-dimensional real time image of tissue-lead interface 310.

Figure 2:
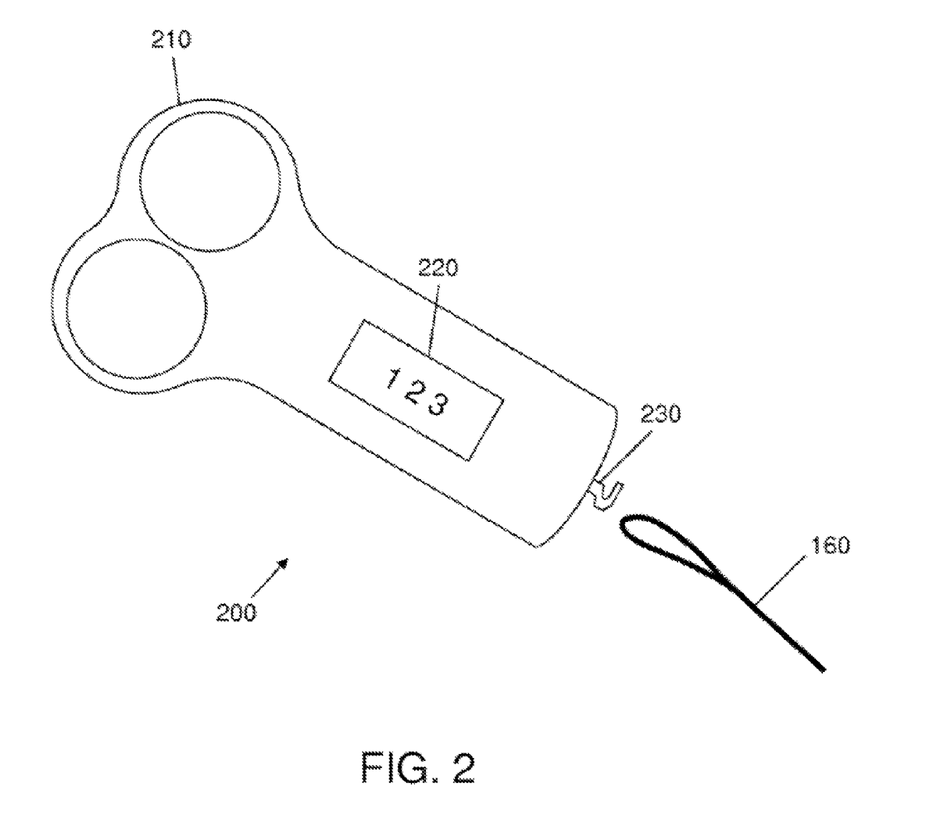
FIG. 2 is a perspective view of a proximal end of the device shown in FIG. 1.

FIG. 2 is a perspective view of a handle device 200 configured to house force gauge 110 (shown in FIG. 1). In the exemplary embodiment, handle device 200 includes a grip 210, a display 220, and a hook 230 configured to couple to stylet 160. In the exemplary embodiment, handle device 200 is configured to facilitate applying a fraction force to stylet 160. More specifically, in the exemplary embodiment, force gauge 110 is configured to measure the traction force applied by handle device 200 to stylet 160.

Figure 3:
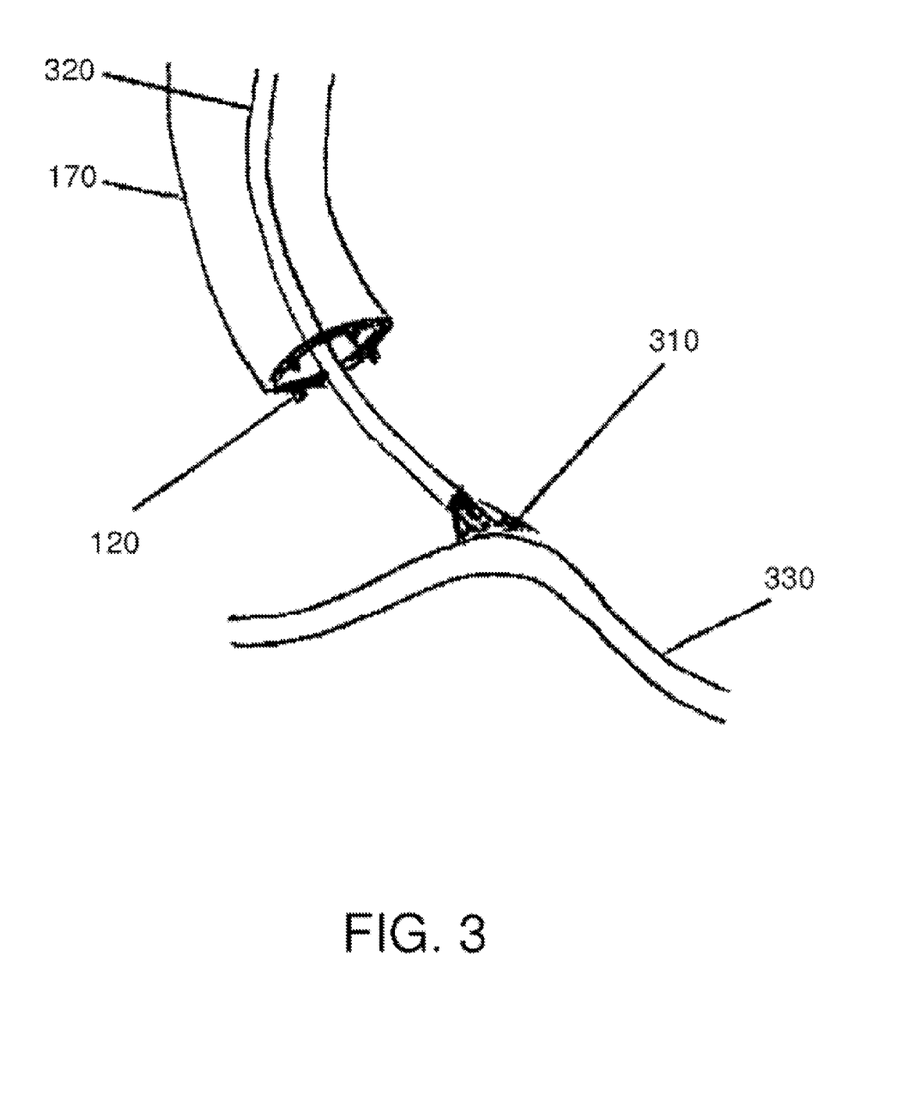
FIGS. 3 and 4 are perspective views of a distal end of the device shown in FIG. 1.
Figure 4:
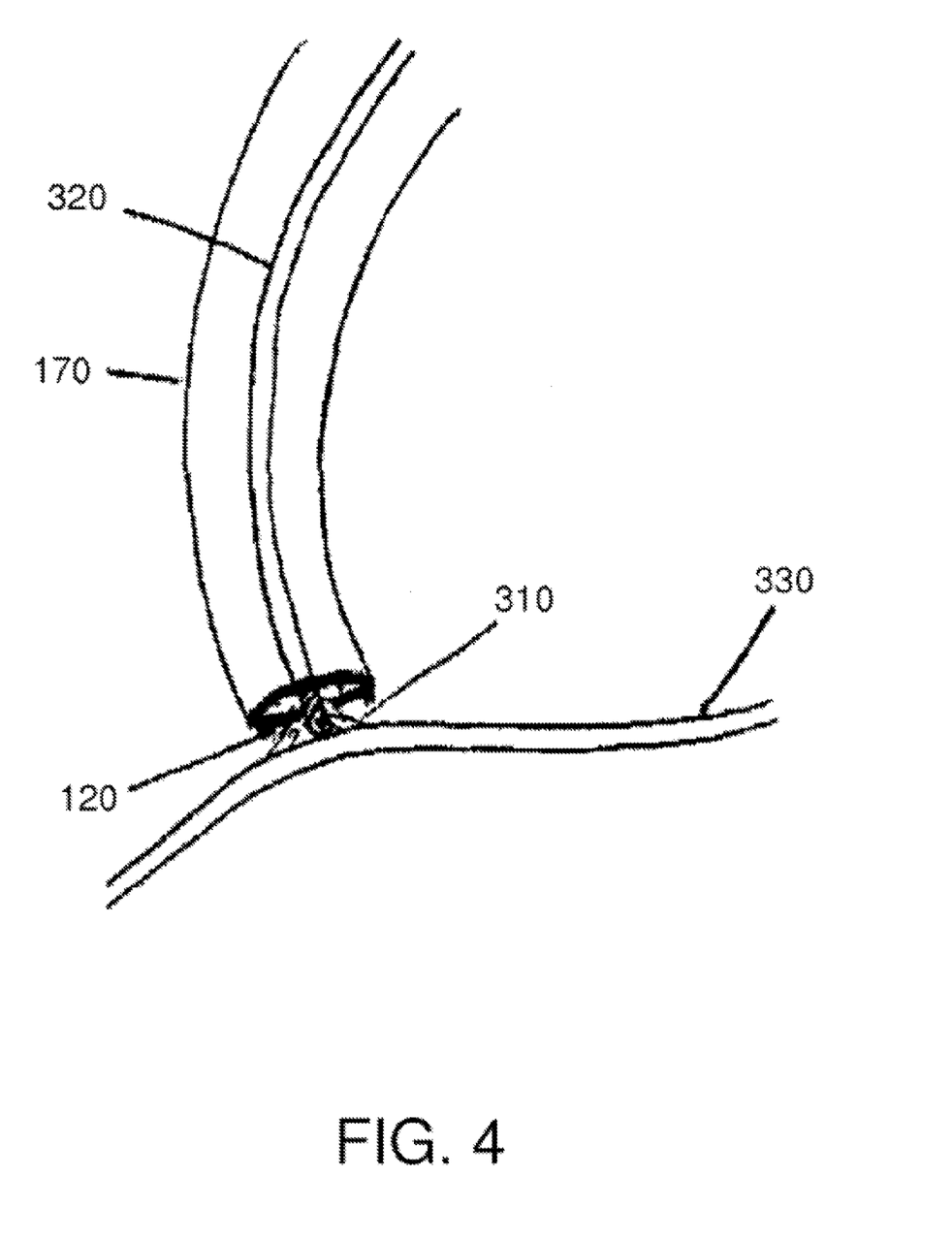

FIGS. 3 and 4 are perspective views of distal end 174 of sheath 170. During use, in the exemplary embodiment, a user operates device 100 to apply a traction force and a countertraction force to lead-tissue interface 310. More specifically, in the exemplary embodiment, the user operates handle device 200 to apply a traction force to lead-tissue interface 310 via stylet 160 and operates sheath 170 to apply a countertraction force about lead-tissue interface 310. As shown in FIG. 4, sheath 170 is coupled to tissue 330 about lead-tissue interface 310 such that sheath 170 may apply a countertraction force to tissue 330 about lead-tissue interface 310 while stylet 160 applies a traction force to lead-tissue interface 310. In the exemplary embodiment, lead-tissue interface 310 includes a scar tissue growth.

In the exemplary embodiment, a traction force and a countertraction force are measured by electrically and/or optically monitoring force gauge 110 and strain gauge 120, respectively, for a change to at least one of a resistance, a conductance, an impedance, and an optical output. In the exemplary embodiment, interface unit 130 is configured to convert the signals received from force gauge 110 and stress gauge 120 to calculate a traction force and a countertraction force, respectively. Moreover, in the exemplary embodiment, interface unit 130 is configured to interpret the calculated forces and present a desired user display based on a predetermined algorithm.

For example, FIGS. 5-8 are graphical representations of different traction forces, countertraction forces, predetermined thresholds, and predetermined ratios. Levels of tension that increase risk of tissue avulsion may be determined by animal tests. These parameters are then used as guidelines for limits of pressure that can be tolerated. In one embodiment, a predetermined force is approximately 2-2.7 N. In another embodiment, an acceptable countertraction force/traction force ratio is approximately 50-100%. In yet another embodiment, an acceptable countertraction force/traction force ratio of is approximately 60-90%. Notably, the thresholds and ratios are not limited to any particular value because several factors should be taken into consideration including a mitral valve annulus diameter, a quantity of sutures, and magnetic forces. Other factors include tissue age, damage, disease, and infection.

Figure 5:
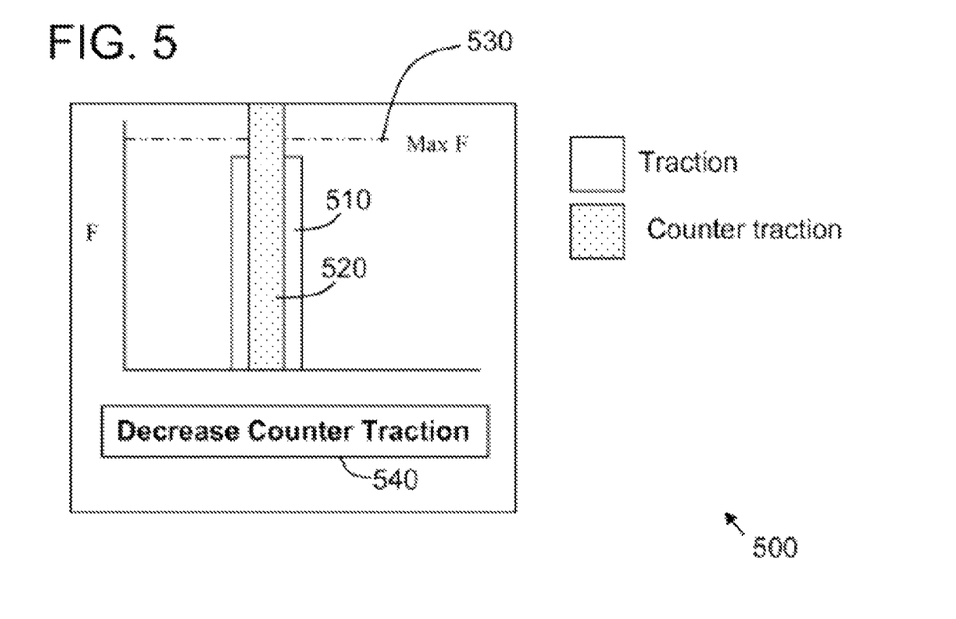
FIGS. 5-8 are graphical illustrations of traction-countertraction.

FIG. 5 is a display 500 that shows a traction force 510, a countertraction force 520, and a predetermined threshold 530. More specifically, display 500 shows traction force 510 below a predetermined threshold 530 and countertraction force 520 above threshold 530. Based on the information shown on display 500, a user should decrease countertraction force 520 to a level that is at least below threshold 530. Display 500 also includes a literal graphic 540 that shows a recommendation based on the fraction force 510, countertraction force 520, and threshold 530.

Figure 6:
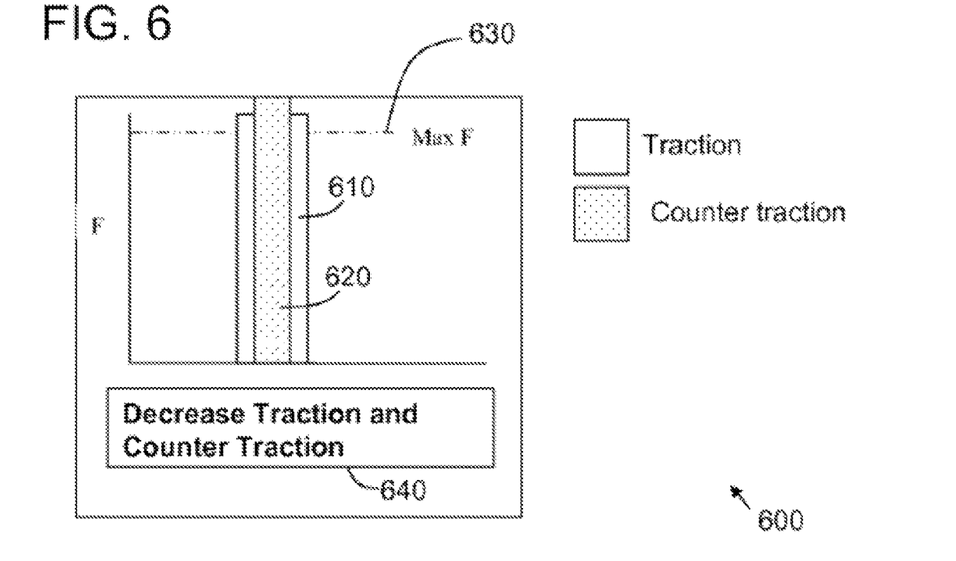

FIG. 6 is a display 600 that shows a traction force 610, a countertraction force 620, and a predetermined threshold 630. More specifically, display 600 shows both traction force 610 and countertraction force 620 above threshold 630. Based on the information shown on display 600, a user should decrease both fraction force 610 and countertraction force 620 to levels that are at least below threshold 630. Display 600 also includes a literal graphic 640 that shows a recommendation based on the traction force 610, countertraction force 620, and threshold 630.

Figure 7:
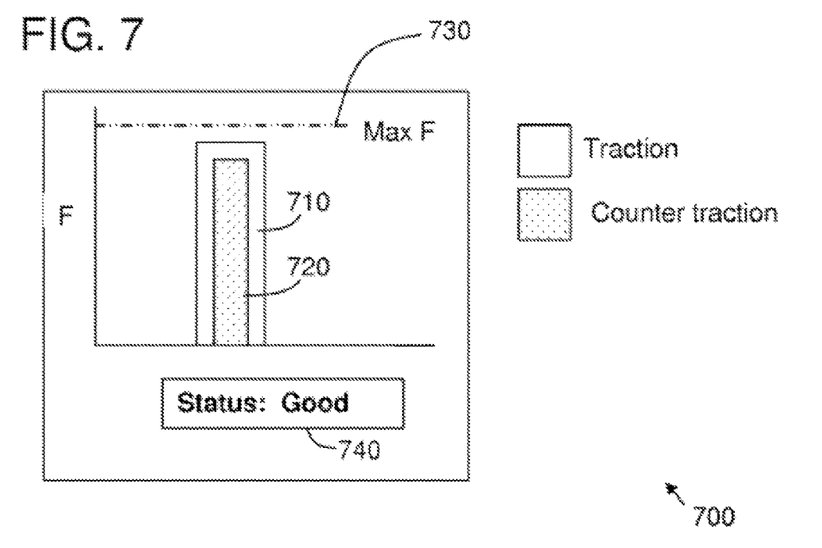

FIG. 7 is a display 700 that shows a traction force 710, a countertraction force 720, and a predetermined threshold 730. More specifically, display 700 shows both traction force 710 and countertraction force 720 below threshold 730. Moreover, a proportion of countertraction force 720 to traction force 710 is of an acceptable ratio. Based on the information shown on display 700, a user should maintain both traction force 710 and countertraction force 720. Display 700 also includes a literal graphic 740 that shows a recommendation based on the traction force 710, countertraction force 720, and threshold 730.

Figure 8:
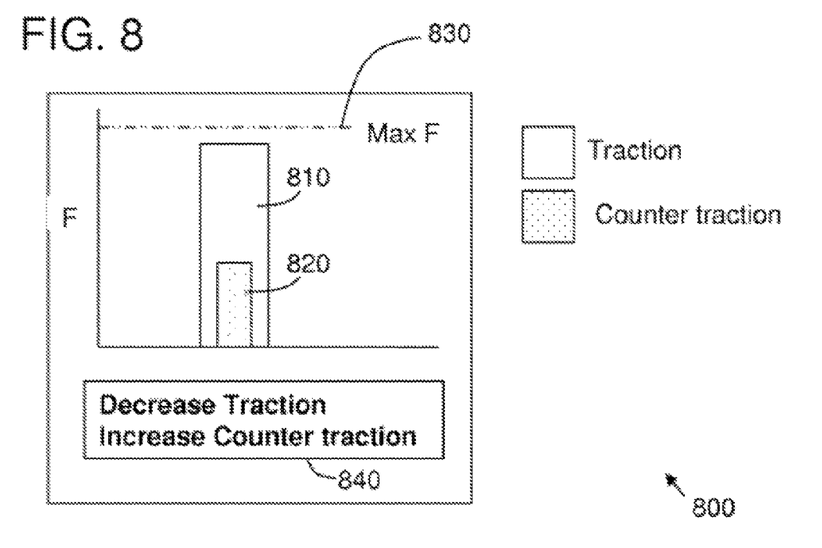

FIG. 8 is a display 800 that shows a traction force 810, a countertraction force 820, and a predetermined threshold 830. More specifically, display 800 shows both traction force 810 and countertraction force 820 below threshold 830. However, a proportion of countertraction force 820 and traction force 810 is not of an acceptable ratio. Based on the information shown on display 800, a user should decrease traction force 810 and/or increase countertraction force 820 to a level that would facilitate maintaining an acceptable ratio. Display 800 also includes a literal graphic 840 that shows a recommendation based on the traction force 810, countertraction force 820, and threshold 830.

For another example, FIGS. 9-12 are graphical representations of different traction forces and countertraction forces over a predetermined period of time. In the exemplary embodiments, data obtained from force gauge 110 and strain gauge 120 is used to provide a continuous record of traction and countertraction forces throughout the duration of a procedure. For example, a final report is created at the end of a procedure to document the changes in traction and countertraction forces that were seen during a particular case.

Figure 9:
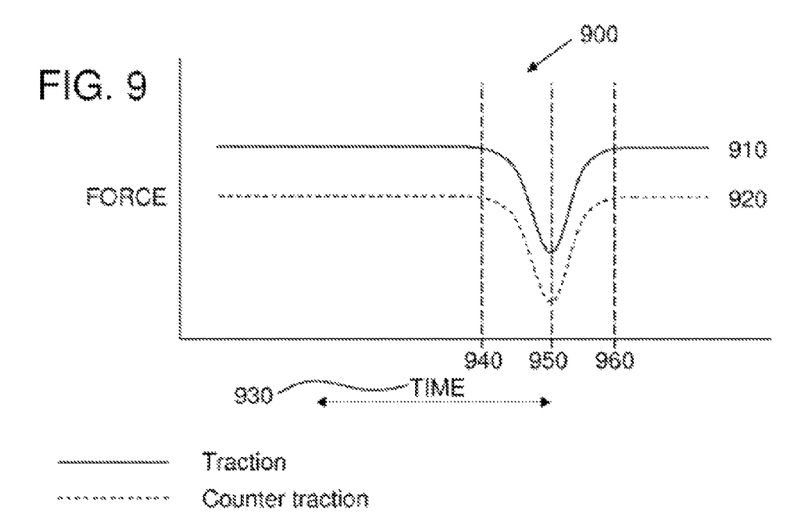
FIGS. 9-12 are graphical illustrations of traction-countertraction for a predetermined period of time.

FIG. 9 is a display 900 that shows a traction force 910 and a countertraction force 920 over a predetermined period of time 930. More specifically, display 900 shows both traction force 910 and countertraction force 920 with a sudden decrease at time 940, a sudden increase at time 950, and are-stabilization at time 960. The information shown on display 900 may indicate that there is an inner core fracture.

Figure 10:
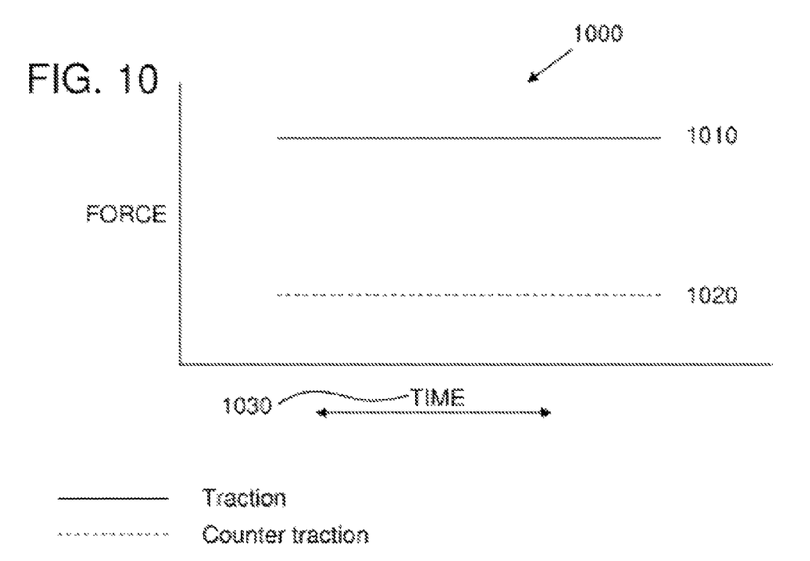

FIG. 10 is a display 1000 that shows a traction force 1010 and a countertraction force 1020 over a predetermined period of time 1030. More specifically, display 1000 shows countertraction force 1020 at a level that is significantly less than traction force 1010. Based on the information shown on display 1000, a user should decrease traction force 1010 and/or increase countertraction force 1020 to a level that would facilitate maintaining an acceptable ratio.

Figure 11:
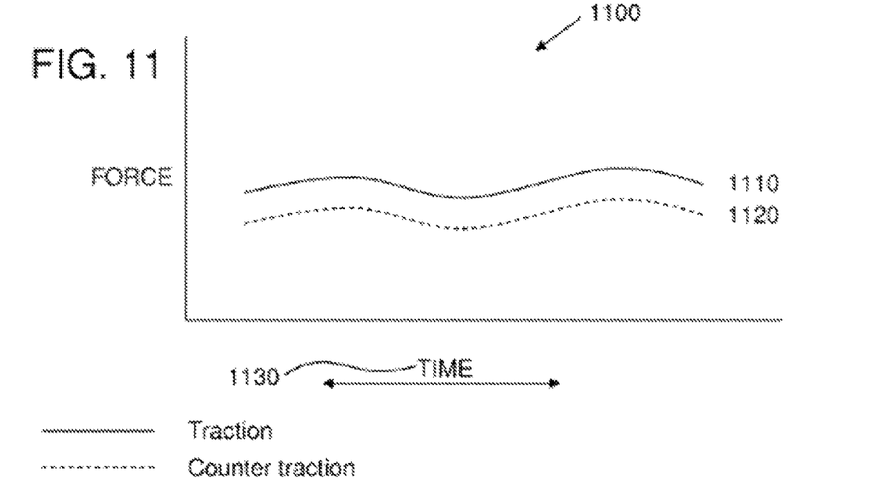

FIG. 11 is a display 1100 that shows a traction force 1110 and a countertraction force 1120 over a predetermined period of time 1130. More specifically, display 1100 shows countertraction force 1120 at an appropriate level relative to fraction force 1110. Based on the information shown on display 1100, a user should maintain both traction force 1110 and countertraction force 1120.

Figure 12:
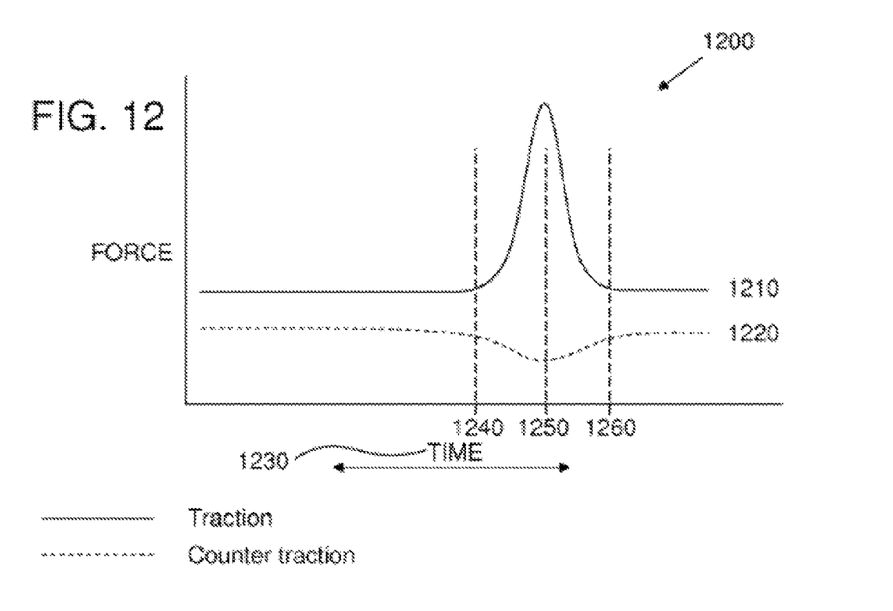

FIG. 12 is a display 1200 that shows a traction force 1210 and a countertraction force 1220 over a predetermined period of time 1230. More specifically, display 1200 shows traction force 1210 with a sudden increase at time 1240, a sudden decrease at time 1250, and a re-stabilization at time 1260 while countertraction force 1220 is at substantially constant level over time 1230. Based on the information shown on display 1200, a user would know that there is an increased risk of tissue avulsion.

In addition to the graphical illustrations shown in FIGS. 5-12, display 180 is configured to present an alert and/or warning by means of audible or visible alarms, such as a blinking light. More specifically, in the exemplary embodiment, display 180 is configured to present an alarm when at least one a traction force and a countertraction force is outside predetermined thresholds and continue to present the alarm until the alert criteria has been corrected. In the exemplary embodiment, a presentation of the alarm facilitates decreasing response time.

For example, in one embodiment, display 180 is a panel that includes two sets lights, a first set of lights for a traction force and a second set of lights for a countertraction force. More specifically, in the one embodiment, display 180 is configured to emit a green color to indicate an appropriate level of force, a yellow color to indicate that force may be increased, and a red color to indicate that a force should be decreased. Based on an assumption that cardiac tissue 330 tears at 2.7 N, in the exemplary embodiment, the appropriate level for the traction force is approximately 1-2 N, and the appropriate level for the countertraction forces is approximately 50-90% of the traction force.

In another embodiment, display 180 is configured to present an audible alarm based on the threshold levels described above. In yet another embodiment, handle 200 is configured to present a tactile signal, including changes in temperature and vibration, based on the threshold levels described above. Coding of the audible alarm and tactile signal may also be achieved by changes in volume, pitch, intensity, and tempo.

Figure 13:
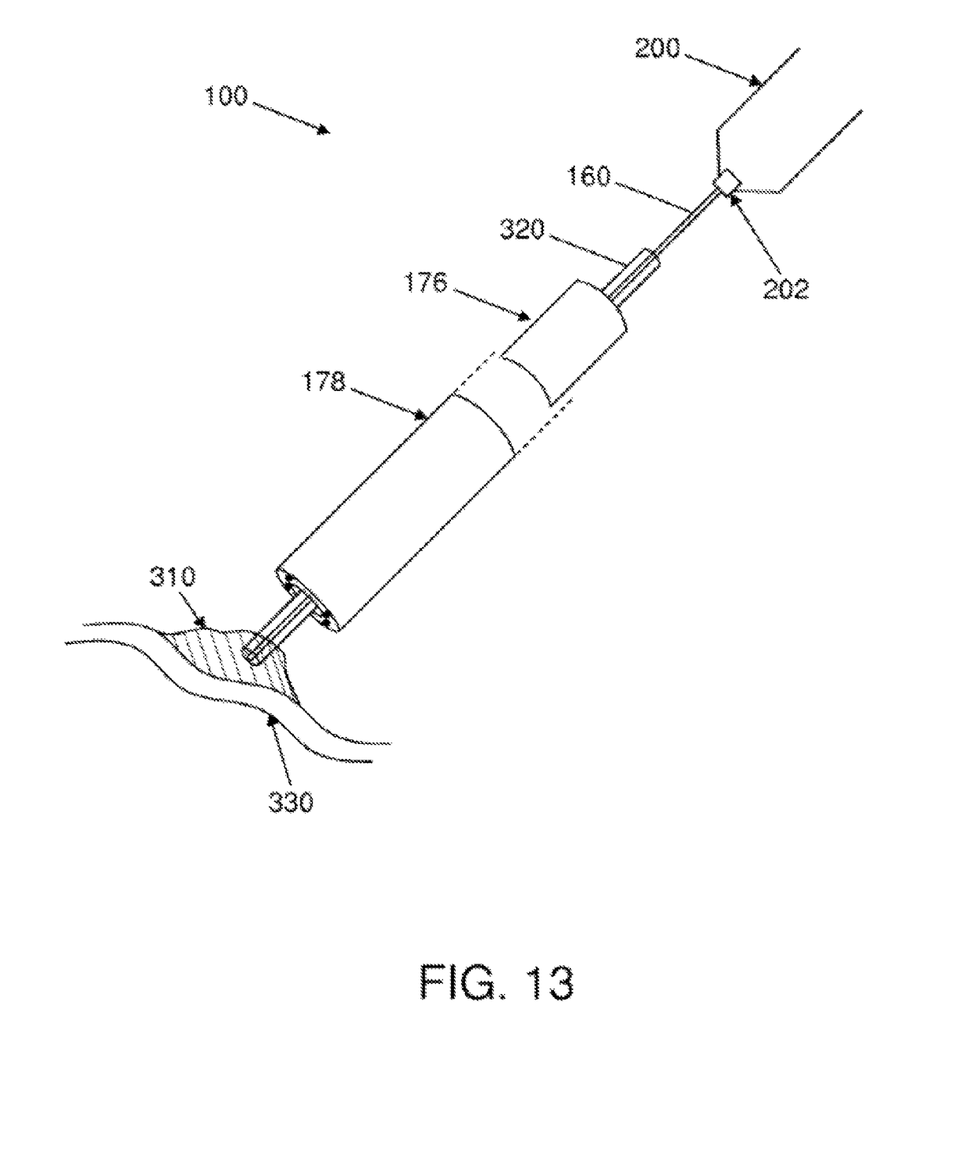
FIG. 13 is another schematic illustration of the device shown in FIG. 1.

FIG. 13 is a schematic illustration of device 100 that includes automatic mechanisms that are configured to reduce at least one of a traction and a countertraction force. In the exemplary embodiment, the automatic mechanisms are release mechanism 202 and sheath 170, wherein sheath 170 includes a first sheath 176 that is coupled to a second sheath 178 such that sheath 170 is used in a telescoping fashion. Notably, the automatic mechanisms are not limited to mechanical mechanisms, but rather may include electronic response systems that are configured to monitor and regulate at least one of a traction force and a countertraction force.

In the exemplary embodiment, release mechanism 202 is configured to release stylet 160 from handle 200 when a traction force exceeds a predefined threshold such that the release facilitates suddenly decreasing the traction force in a controlled manner. More specifically, in the exemplary embodiment, release mechanism 202 is configured to facilitate controllably sliding stylet 160 into a cavity of handle 200 when a traction force exceeds a predefined threshold.

In the exemplary embodiment, sheath 170 is configured to telescopically contract when a countertraction force exceeds a predefined threshold such that the contraction facilitates suddenly decreasing the countertraction force in a controlled manner. More specifically, in the exemplary embodiment, first sheath 176 is configured to slide into second sheath 178 when a countertraction force exceeds a predefined threshold.

In one embodiment, robotic systems (not shown) are configured to control at least one of a traction force and a countertraction force. More specifically, in this embodiment, the robotic systems are programmed with a plurality of automated responses, including closed loop feedback systems, to facilitate monitoring and regulating at least one of a traction force, a countertraction force, and a proportion of the traction force to the countertraction force.

In one embodiment, a computer includes at least some form of computer readable media. By way of example and not limitation, computer readable media may include computer storage media and communication media. Computer storage media may include volatile and nonvolatile, removable and non-removable media implemented in any method or technology that enables storage of information, such as computer readable instructions, data structures, program modules, or other data. Communication media typically embody computer readable instructions, data structures, program modules, or other data in a modulated data signal such as a carrier wave or other transport mechanism and include any information delivery media. Those skilled in the art should be familiar with the modulated data signal, which has one or more of its characteristics set or changed in such a manner as to encode information in the signal. Combinations of any of the above are also included within the scope of computer readable media.

Embodiments of the invention are operational with numerous other general purpose or special purpose computing system environments or configurations. Examples that may be suitable for use with aspects of the invention include, but are not limited to, personal computers, server computers, hand-held or laptop devices, multiprocessor systems, microprocessor-based systems, set top boxes, programmable consumer electronics, mobile telephones, network PCs, minicomputers, mainframe computers, distributed computing environments that include any of the above systems or devices, and the like.

Embodiments of the invention may be described in the general context of computer-executable instructions, such as program modules, executed by one or more controllers, computers, or other devices. Aspects of the invention may be implemented with any number and organization of components or modules. For example, aspects of the invention are not limited to the specific computer-executable instructions or the specific components or modules illustrated in the figures and described herein. Alternative embodiments of the invention may include different computer-executable instructions or components having more or less functionality than illustrated and described herein.

The order of execution or performance of the operations m the embodiments of the invention illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

In some embodiments, a processor includes any programmable system including systems and microcontrollers, reduced instruction set circuits (RISC), application specific integrated circuits (ASIC), programmable logic circuits (PLC), and any other circuit or processor capable of executing the functions described herein. The above examples are exemplary only, and thus are not intended to limit in any way the definition and/or meaning of the term processor.

In some embodiments, a database includes any collection of data including hierarchical databases, relational databases, flat file databases, object-relational databases, object oriented databases, and any other structured collection of records or data that is stored in a computer system. The above examples are exemplary only, and thus are not intended to limit in any way the definition and/or meaning of the term database. Examples of databases include, but are not limited to only including, Oracle® Database, MySQL, IBM® DB2, Microsoft® SQL Server, Sybase®, and PostgreSQL. However, any database may be used that enables the systems and methods described herein. (Oracle is a registered trademark of Oracle Corporation, Redwood Shores, Calif.; IBM is a registered trademark of International Business Machines Corporation, Armonk, New York; Microsoft is a registered trademark of Microsoft Corporation, Redmond, Wash.; and Sybase is a registered trademark of Sybase, Dublin, Calif.)

Technical effects of the methods, systems, and computers described herein include at least one of (a) receiving a traction force; (b) receiving a countertraction force; (c) presenting data regarding at least one of the traction force and the countertraction force; (d) presenting an alert that is at least one of an audible signal, a visual signal, and a tactile signal when at least one of the traction force and the countertraction force exceeds a predetermined threshold; (e) presenting an alert that is at least one of an audible signal, a visual signal, and a tactile signal when a ratio of the countertraction force to the traction force is outside a predetermined range; (f) plotting the data for a predetermined period of time; and (g) displaying an image of a tissue-lead interface.

The methods and systems for the force assessment device and the method for lead extraction described herein enable monitoring traction and countertraction forces, thereby reducing the risk of lead damage, tissue avulsion, and heart wall rupture. More specifically, the force assessment device and the method for lead extraction provides a quantification of traction and countertraction forces, which facilitates reducing variability due to patient-specific characteristics and increasing operator confidence during lead extraction procedures.

Exemplary embodiments of a force assessment device and a method for lead extraction are described above in detail. The methods and systems are not limited to the specific embodiments described herein, but rather, components of the methods and systems may be utilized independently and separately from other components described herein. Moreover, the methods and systems described herein may be used in combination with known methods and systems without need for modification. Further, the present invention can be implemented and utilized in connection with many other industries.

While the invention has been described in terms of various specific embodiments, those skilled in the art will recognize that the invention can be practiced with modification within the spirit and scope of the claims.

What is claimed is:

1. A method for lead extraction, said method comprising:
providing a force gauge;
measuring a traction force with the force gauge;
providing a strain gauge;
measuring a countertraction force with the strain gauge; and
presenting data regarding at least one of the traction force and the countertraction force.

2. A method for lead extraction in accordance with claim 1 further comprising coupling the force gauge to a stylet that is configured to apply the traction force to a tissue-lead interface, wherein the force gauge is at least one of a spring, a fiber optic sensor, a miniature load cell, and a piezoelectric material.

3. A method for lead extraction in accordance with claim 1 further comprising coupling the strain gauge to a sheath that is configured to apply the countertraction force about a tissue-lead interface, wherein the strain gauge is at least one of a spring, a fiber optic sensor, a miniature load cell, and a piezoelectric material.

4. A method for lead extraction in accordance with claim 1 further comprising presenting an alert that is at least one of an audible signal, a visual signal, and a tactile signal when at least one of the traction force and the countertraction force exceeds a predetermined threshold.

5. A method for lead extraction in accordance with claim 1 further comprising presenting an alert that is at least one of an audible signal, a visual signal, and a tactile signal when a ratio of the countertraction force to the traction force is outside a predetermined range.

6. A method for lead extraction in accordance with claim 1 further comprising plotting the data for a predetermined period of time.

7. A method for lead extraction in accordance with claim 1 further comprising displaying an image of a tissue-lead interface.

8. A method for lead extraction, the method comprising:
providing a stylet and a force gauge coupled to the stylet;
measuring a traction force via the force gauge while applying the traction force to a tissue-lead interface via the stylet;
measuring a countertraction force; and
presenting data regarding at least one of the traction force and the countertraction force.

9. A method for lead extraction in accordance with claim 8, further comprising presenting an alert that is at least one of an audible signal, a visual signal, and a tactile signal when at least one of the traction force and the countertraction force exceeds a predetermined threshold.

10. A method for lead extraction in accordance with claim 8, further comprising presenting an alert that is at least one of an audible signal, a visual signal, and a tactile signal when a ratio of the countertraction force to the traction force is outside a predetermined range.

11. A method for lead extraction in accordance with claim 8, wherein the force gauge is at least one of a spring, a fiber optic sensor, a miniature load cell, and a piezoelectric material.

12. A method for lead extraction in accordance with claim 8, further comprising:
providing a sheath and a strain gauge coupled to the sheath; and
measuring the countertraction force via the strain gauge while applying the countertraction force to a tissue-lead interface via the sheath.

13. A method for lead extraction in accordance with claim 12, wherein the strain gauge is at least one of a spring, a fiber optic sensor, a miniature load cell, and a piezoelectric material.

14. A method for lead extraction in accordance with claim 8, wherein the stylet is a locking stylet.

15. A method for lead extraction in accordance with claim 8, further comprising automatically reducing the traction force when the traction force exceeds a predetermined threshold.

16. A method for lead extraction, the method comprising:
providing a force assessment device comprising:
a stylet;
a force gauge coupled to the stylet, wherein the force gauge is at least one of a spring, a fiber optic sensor, a miniature load cell, and a piezoelectric material;
a strain gauge;
an interface communicatively coupled to the force gauge and the strain gauge;
measuring a traction force with the force gauge while applying the traction force to a tissue-lead interface via the stylet;
measuring a countertraction force with the strain gauge; and
presenting data regarding at least one of the traction force and the countertraction force via the interface.

17. A method for lead extraction in accordance with claim 16, wherein the force assessment device further comprises a sheath coupled to the strain gauge, and further comprising measuring the countertraction force via the strain gauge while applying the countertraction force to a tissue-lead interface via the sheath.

18. A method for lead extraction in accordance with claim 17, wherein the strain gauge is at least one of a spring, a fiber optic sensor, a miniature load cell, and a piezoelectric material.

19. A method for lead extraction in accordance with claim 16, further comprising presenting an alert via the interface that is at least one of an audible signal, a visual signal, and a tactile signal when at least one of the traction force and the countertraction force exceeds a predetermined threshold.

20. A method for lead extraction in accordance with claim 16, further comprising presenting an alert via the interface that is at least one of an audible signal, a visual signal, and a tactile signal when a ratio of the countertraction force to the traction force is outside a predetermined range.

* * * * *

UNITED STATES PATENT AND TRADEMARK OFFICE
CERTIFICATE OF CORRECTION

PATENT NO. : 9,414,783 B2
APPLICATION NO. : 14/691357
DATED : August 16, 2016
INVENTOR(S) : Verma Page 1 of 1

It is certified that error appears in the above-identified patent and that said Letters Patent is hereby corrected as shown below:

In the Specification

Column 1, Line 5, delete "2009," and insert -- 2009, now Pat. No. 9,032,806, --

Column 3, Lines 64-65, delete "transespohageal" and insert -- transesophageal --

Column 4, Line 6, delete "fraction" and insert -- traction --

Column 4, Line 30, delete "stress gauge 120" and insert -- strain gauge 120 --

Column 4, Line 60, delete "fraction" and insert -- traction --

Column 4, Line 67, delete "fraction" and insert -- traction --

Column 5, Line 42, delete "are-stabilization" and insert -- a re-stabilization --

Column 5, Line 55, delete "fraction" and insert -- traction --

Signed and Sealed this
First Day of January, 2019

Andrei Iancu
*Director of the United States Patent and Trademark Office*